US00PP37610P2

(12) United States Plant Patent
Wyckstandt

(10) Patent No.: US PP37,610 P2
(45) Date of Patent: Aug. 18, 2026

(54) ***AGAPANTHUS* PLANT NAMED 'A22004'**

(50) Latin Name: ***Agapathus* hybrid**
Varietal Denomination: A22004

(71) Applicant: Tim Wyckstandt, Aalter (BE)

(72) Inventor: Tim Wyckstandt, Aalter (BE)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/422,445

(22) Filed: Dec. 17, 2025

(30) Foreign Application Priority Data

Jul. 29, 2025 (QZ) ..... PBR 20251685

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
CPC ..... A01H 5/02; A01H 5/00; A01H 6/04
See application file for complete search history.

(56) References Cited

U.S. PATENT DOCUMENTS

PP25,401 P2 * 3/2015 Rijnbeek ..... Plt./398

* cited by examiner

*Primary Examiner* — June Hwu
(74) *Attorney, Agent, or Firm* — Penny J. Aguirre

(57) ABSTRACT

A new cultivar of *Agapanthus* plant named 'A22004' that is characterized by its floriferous and long flowering period with repeat blooming, its violet-blue flowers with a darker central stripe on the tepals, and its compact plant habit with a tall plant height (average of 60 cm in height).

3 Drawing Sheets

Botanical classification: *Agapanthus* hybrid.
Varietal denomination: 'A22004'.

CROSS REFERENCE TO RELATED APPLICATIONS

This application claims priority to European Community Plant Variety Office (CPVO) Plant Breeder's Rights Application No. 2025/1685, filed Jul. 29, 2025. The Applicant received the information for the Plant breeders' rights application directly from the Inventor. This application is co-pending with a U.S. Plant Patent Applications filed for a plant patent derived from the same breeding program that is entitled *Agapanthus* Plant Named 'A19002' (U.S. Plant patent application Ser. No. 19/422,442), *Agapanthus* Plant Named 'A21001' (U.S. Plant patent application Ser. No. 19/422,443), *Agapanthus* Plant Named 'Su Casa' (U.S. Plant patent application Ser. No. 19/422,434), and *Agapanthus* Plant Named 'Vitro 002' (U.S. Plant patent application Ser. No. 19/422,451).

BACKGROUND OF THE INVENTION

The present invention relates to a new and distinct cultivar of *Agapanthus* of hybrid origin and will be referred to hereafter by its cultivar name, 'A22004'. 'A22004' represents a new perennial grown for landscape and container use.

'A22004' was discovered in July of 2021 as a single unique plant by the Inventor from amongst seedlings in a trial field in Aalter, Belgium. The trial field had been planted with numerous unpatented and unnamed proprietary plants from the Inventor's breeding program. The parents are therefore unknown.

Asexual propagation of the new cultivar was first accomplished by division by the Inventor in Aalter, Belgium in March of 2023. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'A22004' as a distinct cultivar of *Agapanthus*.

1. 'A22004' exhibits a floriferous and long flowering period with repeat blooming.
2. 'A22004' exhibits violet-blue flowers with a darker central stripe on the tepals.
3. 'A22004' exhibits a compact plant habit with a tall plant height (average of 60 cm in height).

'A22004' can be most closely compared to the *Agapanthus* cultivars 'Andbin' (U.S. Plant Pat. No. 26,336) and 'Lapis Lazuli' (not patented). 'Andbin' is similar to 'A22004' in having blue flowers and repeat blooming. 'Andbin' differs from 'A22004' in having less intense blue colored flowers with no central stripe, a less floriferous blooming habit, and shorter blooming period. 'Lapis Lazuli' is similar to 'A22004' in having blue flowers and a compact plant habit with a similar plant height. 'Lapis Lazuli' differs from 'A22004' in having smaller inflorescences and less intense colored violet-blue flowers.

'A22004' can also be compared to the co-pending cultivars of *Agapanthus*; 'A19002', 'A21001', 'Su Casa' and 'Vitro 002'. 'A19002' differs from 'A22004' in having white flowers. 'A21001' differs from 'A22004' in having deep blue flowers with blue filaments. 'Su Casa' differs from 'A22004' in having light violet-blue flowers. 'Vitro 002' differs from 'A22004' in having white flowers with yellow filaments.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the effective filing date. Disclosures include website listings by van Vliet New Plants.

BRIEF DESCRIPTION OF THE DRAWINGS

The accompanying color photographs illustrate the overall appearance and distinct characteristics of the new *Agapanthus*. The photographs were taken of a plant 19 months in age of 'A22004' as grown in an unheated poly-covered tunnel in a 19-cm container in Aalter, Belgium.

The photograph in FIG. 1 provides a side view of a plant of 'A22004' in bloom.

Figure 1:
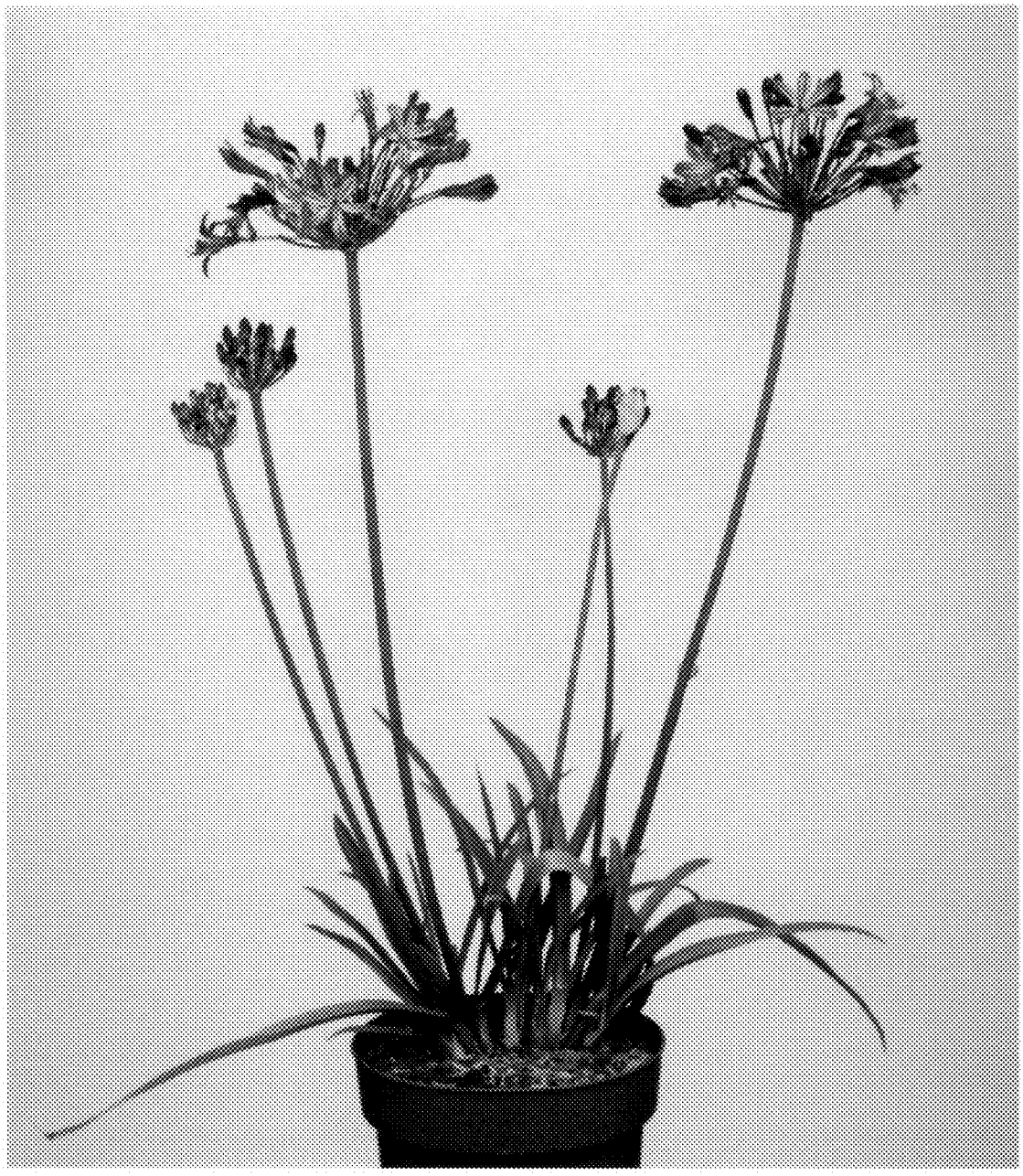
Figure 2:
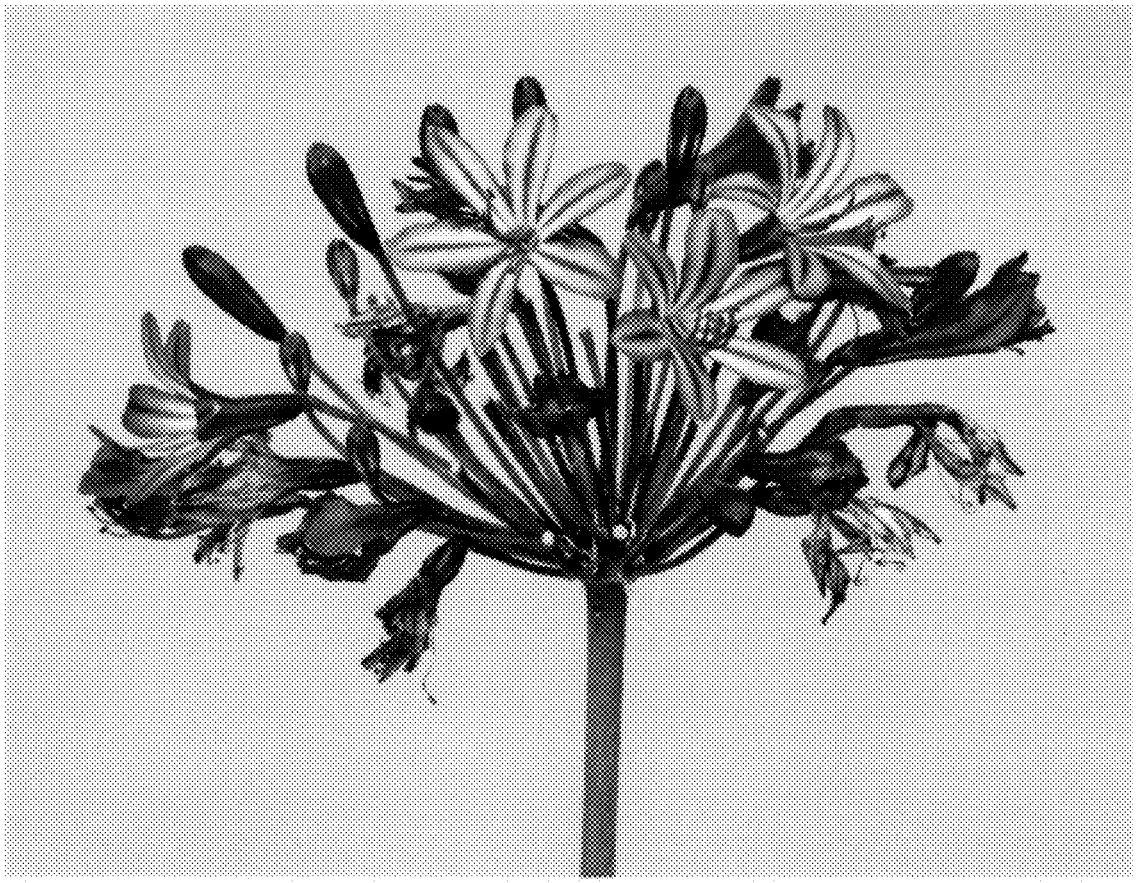

The photograph in FIG. 2 provides a close-up view of an inflorescence of 'A22004'.

Figure 3:
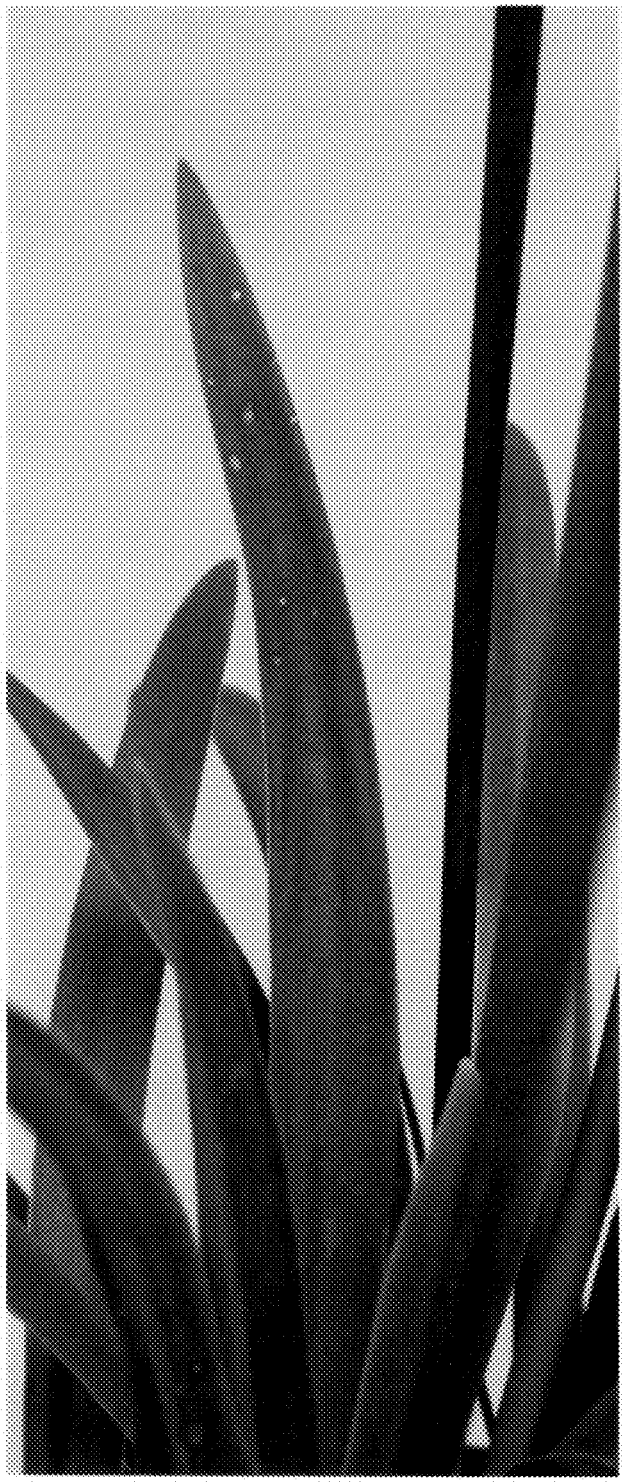

The photograph in FIG. 3 provides a close-up view of the foliage of 'A22004'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 19-month-old plants of 'A22004' as grown in an unheated poly-covered tunnel in 19-cm containers in Aalter, Belgium. The phenotype of the new cultivar may vary with variations in environmental, climatic, and cultural conditions, as it has not been tested under all possible environmental conditions. The color determinations are in accordance with The 2015 (2019 reprint) Colour Chart of The Royal Horticultural Society, London, England, except where general color terms of ordinary dictionary significance are used.

General description:

- *Blooming period.*—End of May into November in Belgium.
- *Plant type.*—Semi-deciduous (climate dependent) herbaceous perennial.
- *Plant habit.*—Basal rosettes with inflorescences emerging from the rosette center.
- *Height and spread.*—Average of 60 cm in height and 50 cm in spread as a plant grown in the landscape.
- *Hardiness.*—At least in U.S.D.A. Zones 8 to 12.
- *Diseases and pests.*—No susceptibility or resistance to diseases or pests has been observed.
- *Root description.*—Thick and fleshy.
- *Propagation.*—Division and tissue culture.

Foliage description:

- *Leaf shape.*—Ligulate.
- *Leaf division.*—Simple.
- *Leaf base.*—Decurrent, broadly cuneate.
- *Leaf apex.*—Acute.
- *Leaf aspect.*—Moderately carinate, slightly to moderately curved.
- *Leaf venation.*—Parallel, upper surface; 143A, lower surface; 145C, secondary veins 137B.
- *Leaf margins.*—Entire.
- *Leaf size.*—Up to 18.8 cm in length and up to 1.4 cm in width.
- *Leaf surface.*—Both surfaces non-rugose, upper surface slightly glossy, lower surface very slightly glossy.
- *Leaf number.*—Average of 7 leaves per rosette.
- *Foliage density.*—Medium.
- *Leaf color.*—Young leaves upper surface; 143A, center and base 145D, young leaves lower surface; 144A, center 144A, base 145C, mature leaves upper and lower surface; 144A.
- *Leaf attachment.*—Sessile to base.

Flower description:

- *Inflorescence type.*—Umbel, hemispherical.
- *Flower fragrance.*—None.
- *Flower type.*—Rotate, campanulate, base of tepals fused.
- *Flower number.*—An average of 55 flowers per umbel, 380 buds and flowers per plant.
- *Inflorescence size.*—Average of 9.9 cm in height, 15.3 cm in diameter.
- *Flower size.*—An average of 2.9 cm in depth, 3.5 cm in diameter, throat 3 mm in diameter, tube; 1 cm in length and 4.5 mm in diameter.
- *Lastingness of inflorescence.*—10 days, self-cleaning.
- *Flower aspect.*—Primarily upright to pedicel.
- *Peduncle.*—1 per rosette, very sturdy, oval in shape, held primarily upright 57.5°, surface is glabrous, slightly glaucous and moderately glossy, average of 47.2 cm in length and 5 mm in width, color; a blend of 144A and 146B, thin waxy glaucous layer 193D.
- *Pedicels.*—Oval in shape, held in multiple angles, surface is glabrous, glossy, average of 4.5 cm in length and 1 mm, 143A in color.
- *Flower buds.*—Oblanceolate in shape, matte surface, slightly velvety, average of 2.1 cm in length and 7 mm in width, color; N89C, axially striped N92D, lower half N155A.
- *Tepals (perianth).*—6, 2 whorls (3 upper and 3 lower), rotate, oblanceolate in shape, fused base, entire margins, apex; lower tepals acute, upper tepals bluntly acute, surface all tepals; glabrous, slightly velvety, non-rugose, thick substance, size; upper and lower tepals 3 cm in length, lower tepal 5 mm in width, upper tepal 7 mm in width, color (all tepals); when opening upper surface; 92B, base N155A, darker longitudinal central stripe and margins N89C, when opening lower surface; N89C, darker longitudinal central stripe 93A, fully open upper surface; 92B, base NN155D, darker longitudinal central stripe N89B, outside edges N89D, fading to 83B, stripe 83A, fully open lower surface; 94A and 94B, darker longitudinal central stripe 93A, fading to 83B, stripe 83A, base N92C, throat; N155A, tube; 93A with edges between tepals N155A.
- *Bracts.*—Immature inflorescence bract: 1 bract, dropped when individual flowers develop to open, broadly ovate in shape, 3.3 cm in length, 2.6 cm in width, color; upper surface 158A, striped 164A, lower surface 158C, striped 164B, pedicel bract: a single bract at base of pedicel, filiform in shape, 2 cm in length, 0.5 mm in width, color; 165D, striped 165C.

Reproductive organs:

*Gynoecium*.—Pistil; 1, average of 1.6 cm in length, stigma; club-shaped, 88A in color, style; 1.5 cm in length, 88A in color, ovary; oblong in shape, 1 cm in length, 4 mm in width and N144B in color, pistil lodes not present.

*Androecium*.—Stamens; 6, anthers; basifixed, oblong in shape, 5 mm in length, 1.5 mm in width, N186A in color, filament; 2.1 cm in length, color; 90B, base 91B, pollen; moderate in quantity and 160A in color, staminodes not present.

*Fruit/seed*.—None observed to date.

It is claimed:

1. A new and distinct cultivar of *Agapanthus* plant named 'A22004' as herein illustrated and described.

* * * * *